United States Patent [19]
Murphy

[11] Patent Number: 5,635,196
[45] Date of Patent: Jun. 3, 1997

[54] METHOD FOR PREPARING A DISINFECTING AND GELLING COMPOSITION AND RESULTING COMPOSITION

[76] Inventor: William J. Murphy, 620 Woodland Ave., Hinsdale, Ill. 60521

[21] Appl. No.: 510,404

[22] Filed: Aug. 2, 1995

Related U.S. Application Data

[63] Continuation of Ser. No. 164,383, Dec. 9, 1993, abandoned.

[51] Int. Cl.$^6$ ................................................ A01N 25/10
[52] U.S. Cl. ...................... 424/409; 424/421; 424/76.5; 424/76.8; 514/705
[58] Field of Search ........................ 424/405, 406, 424/409, 417, 419–421, 489, 76.8–76.5

[56] References Cited

U.S. PATENT DOCUMENTS

| | | | |
|---|---|---|---|
| 3,661,815 | 5/1972 | Smith | 525/54.32 |
| 4,112,192 | 9/1978 | Fellows | 424/333 |
| 4,302,369 | 11/1981 | Elmquist | 524/734 |
| 4,748,069 | 5/1988 | Cullen | 428/195 |
| 4,749,600 | 6/1988 | Cullen et al. | 428/34.3 |
| 4,816,307 | 3/1989 | Honeycutt | 428/34.1 |
| 4,900,500 | 2/1990 | Honeycutt | 264/263 |
| 5,092,858 | 3/1992 | Benson et al. | 604/319 |
| 5,158,778 | 10/1992 | Donovan et al. | 424/488 |
| 5,279,602 | 1/1994 | Middaugh et al. | 604/320 |
| 5,284,621 | 2/1994 | Kaufman | 422/32 |
| 5,307,819 | 5/1994 | Trautmann et al. | 128/767 |

FOREIGN PATENT DOCUMENTS

| | | |
|---|---|---|
| 0440962 | 8/1991 | European Pat. Off. . |
| 0494599 | 7/1992 | European Pat. Off. . |

*Primary Examiner*—Neil S. Levy
*Attorney, Agent, or Firm*—Tilton, Fallon, Lungmus & Chestnut

[57] ABSTRACT

The method of disinfecting and solidifying an aqueous liquid medical waste containing microorganisms is provided in which dry glutaraldehyde is used as the disinfectant. In preparing the product for use in the method dry glutaraldehyde is mixed with a superabsorbant to partially transfer an aqueous solution from the dry glutaraldehyde to the superabsorbant.

8 Claims, No Drawings

METHOD FOR PREPARING A DISINFECTING AND GELLING COMPOSITION AND RESULTING COMPOSITION

RELATED APPLICATION

This application is a continuation of application Ser. No. 08/164,383, filed Dec. 9, 1993 abandoned.

FIELD OF INVENTION

The field of this invention is the treatment of liquid wastes to improve the convenience and safety of their disposability. In particular this invention is concerned with the use of compositions to solidifying and/or disinfect hospital wastes such as blood and body fluids resulting from surgery, and medical laboratory wastes, all of which are potentially infectious.,

BACKGROUND OF INVENTION

The class of materials known as superabsorbents have been used for converting liquid medical wastes into a gelled or solidified form for disposal. A granular superabsorbent is added to the medical waste, which may be an inadvertent spill or a containerized waste, such as blood or body fluids.

Superabsorbents are polymers which are characterized by their capacity to imbibe water. As the water is absorbed, the superabsorbent swells with a great increase in volume and forms a gel-like material. This class of superabsorbents has been defined as polymers capable of at least a tenfold absorption of aqueous fluid. Two well known kinds of such polymers are the polyacrylates, such as sodium or potassium polyacrylate, and starch-based superabsorbents that comprise starch acrylonitrile graft polymers.

For disinfecting and gelling medical wastes, antimicrobial agents have been used in combination with the superabsorbents. However, a number of practical problems have been encountered in the use of such absorbent/disinfectant mixtures. It is desired to gel the liquid waste while at the same time effectively disinfecting the gelled body throughout its mass. Heretofore, these combined objectives have not been adequately achieved. The efforts or prior inventors are illustrated by U.S. Pat. Nos. 4,748,069, 4,749,600, 4,816, 307, and 4,900,500, and published European application 0440962A2.

When a mixture of a disinfectant powder and a granular absorbent is added to a containerized liquid waste it settles to the bottom before the gellation takes place. The superabsorbent granules then swell and distribute upwardly until the entire liquid is converted to gel form. However, the disinfectant tends to stay in the bottom portion of the container and is not effectively distributed throughout its upper portions. The resulting gelled body, consequently, has an uneven distribution of the disinfectant.

SUMMARY OF INVENTION

The present invention comprises a novel method and composition for disinfecting and solidifying liquid medical wastes. The method and composition are particularly adapted for use with containerized wastes, such as the blood or other body fluids collected in suction canisters during surgical procedures, liquid containerized and other containerized wastes which may contain harmful microorganisms, and medical laboratory wastes. The composition can also be used for hospital application to medical wastes which have spilled on hospital surfaces such as floors and counters. Veterinary medical uses are also envisioned. The method and composition of the invention can be used to sanitize, disinfect and sterilize liquid waste that may contain potential pathogens (bacterial, viral, fungal and parasitic). The invention can also be used to control or reduce odors produced in liquid waste by micro-organisms.

This invention provides improvements over the prior art methods of disinfecting and solidifying aqueous liquid medical wastes. An important feature of the invention is the use of a glutaraldehyde source material which consists essentially of particles of a non-swelling absorbent that has been impregnated with a concentrated aqueous solution of glutaraldehyde. The particles of this source material are externally dry and free-flowing, and can be mixed with a granular superabsorbent. During the mixing a significant interaction occurs.

By mixing together the dry glutaraldehyde source material and a superabsorbent polymer, the glutaraldehyde source material is brought into intimate contact with the superabsorbent. Although the glutaraldehyde and water are tenaciously retained in carrier desiccant particles, the water absorbency of the superabsorbent granules results in a partial transfer of the glutaraldehyde solution. Moreover, this transfer of glutaraldehyde can be carried out without swelling the superabsorbent granules to a non-free-flowing condition. The resulting mixture can be added to the top of a containerized quantity of a liquid waste, such as a surgical or medical laboratory waste, to overcome the poor distribution problem described above. Although the mixture does drop to the lower portion of the container, because of the pre-transfer of the glutaraldehyde to the superabsorbent granules, the disinfectant is effectively distributed in association with the expanding and gelling superabsorbent.

DETAILED DESCRIPTION

Glutaraldehyde is an amber liquid at room temperature. It is soluble in water and alcohols. The present invention, does not directly utilize a solution of glutaraldehyde. Rather, a glutaraldehyde source material is obtained or prepared which consists essentially of particles of a non-swelling desiccant which have been impregnated with a concentrated aqueous solution of glutaraldehyde. The desiccant particles externally remain free-flowing. By way of specific example, an impregnated desiccant product is sold commercially as a "dry glutaraldehyde" by Thetford Corporation, Ann Arbor, Michigan. This product is understood to contain, on a weight basis, approximately 31% glutaraldehyde, 31% water, and 38% desiccant (amorphous silicon dioxide). Desiccants suitable for use in preparing dry glutaraldehyde can be obtained from commercial sources. For example, the "Syloid" amorphous silicas of W. R. Grace & Co., Baltimore, Md., can be used. These products are supplied in the form of powders having a high degree of water absorbancy. In preparing a dry glutaraldehyde, the desiccant particles after impregnation can be formed into granular aggregates. The dry glutaraldehyde product of Thetford, referred to above, is in the form of granular aggregates of 0.5 to 4 mm diameter. Other silica-based desiccants are available commercially, such as the calcium silicate product of J. M. Huber Corp., Harve de Grace, Maryland, sold under the name "Hubersorb". Suitable desiccants are typically amorphous forms of silica which are microporous and have high water absorbancy due to capillary action.

The superabsorbent is used in the form of dry free-flowing granules. Such products are available commercially from a number of sources. One preferred superabsorbent is the potassium polyacrylate superabsorbent sold by Chemdal Corp., Palatine, Ill., as "Aridall 1440". This product is readily water-wettable, and quickly forms a gel on absorbing water. Polyacrylate polymer superabsorbent can also be used in the sodium form, such as the "Aridall 1465" of Chemdal Corp. or "Water Lock" J-550 sodium polyacrylate of Grain Processing Corp., Muscatine, Iowa. Other usable superabsorbents include starch-polyacrylonitrile graft copolymers. For example a starch graft copolymer is sold under the name "Sta-Wet" by Polysorb, Inc., Coeur d'Alene, ID. Chemically this produce is starch-g-poly (acrylamide-co-potassium acrylate). These polymers can be in the form of their sodium or other alkali metal salts, and are further described in U.S. Pat. Nos. 3,661,815 and 4,302,369. Another usable superabsorbent is sold as "Water Lock" G-400 by Grain Processing Corp. This polymer chemically is understood to be the sodium salt of poly(2-propenamide-co-2-propenoic acid). Sodium carboxymethyl cellulose may be modified by aluminum cross-linking to provide a gelling superabsorbent, such as the "AQU-D3236 or D3273" aluminum crosslinked sodium carboxymethyl cellulose products sold by Aqualon, Wilmington, Del.

In preparing the composition of this invention, the desiccant containing the glutaraldehyde is mixed with the granular superabsorbent under conditions resulting in part of the glutaraldehyde being transferred to the superabsorbent. The relative proportions of the ingredients are of importance. Excessive amounts of the glutaraldehyde source material may result in the transfer of so much water that the superabsorbent granules become sticky and non-free flowing. If too little glutaraldehyde material is present, there will be an insufficient transfer of the glutaraldehyde. In general, from about 50 to 300 parts by weight of the glutaraldehyde source material can be mixed per 100 parts of the superabsorbent while achieving the desired results. Preferred proportions are from 100 to 200 parts by weight of the glutaraldehyde material per 100 parts of the absorbent polymer. For example, in a specific embodiment, 3 parts of the dry glutaraldehyde are mixed with 2 parts of the polymer.

In carrying out the transfer of glutaraldehyde to the granules of the superabsorbent it is important, as indicated above, to avoid swelling of the superabsorbent free-flowing granular and/or powder mixture. The mixture should not be so sticky that it is not free-flowing. The mixture should remain free-flowing. Within the proportions described, and depending on the kind and extent of mixing, the amount of water transferred with the glutaraldehyde can be limited so that it does not cause the absorbent granules to become non-free-flowing. It is preferred to have the desiccant carrier impregnated with a concentrated aqueous solution of glutaraldehyde. For example, a 50% aqueous solution can be used, or, more generally, a solution of from 25 to 75% glutaraldehyde can be used for the impregnation.

When the glutaraldehyde source material is obtained in the form of granular aggregates, it can be partially or even completely broken down to powder form comprising individual particles. The particle powder form can assist the contacting. Preferably, however, the granular aggregate material, such as the dry glutaraldehyde supplied by Thetford, is initially processed so that only part of the granules are reduced to a powder. This mixed granule/powder substrate is especially desirable for the controlled transfer contacting.

It has also been found advantageous to add a small amount of non-impregnated, non-swelling desiccant powder in the initial processing of the glutaraldehyde source material. For example, 1 part by weight of a desiccant powder can be mixed with from 40 to 100 parts of the dry glutaraldehyde. For example, in a preferred embodiment, 1 part of an amorphous calcium silicate desiccant is mixed per 60 to 70 parts of the dry glutaraldehyde. Other silicate or silica desiccants can be substituted, such as those described above for absorbing the aqueous solutions of glutaraldehyde.

In the pre-mixing of the glutaraldehyde granules, the added desiccant powder acts as a blending agent. Any moisture released from the glutaraldehyde material can be absorbed by the added desiccant. The initial glutaraldehyde/desiccant mixture can be stored for a short time to allow equilibration to occur. The presence of the added desiccant in the premix also tends to assure that the ingredients remain free-flowing during the transfer of the glutaraldehyde solution.

The use of this invention in a presently preferred embodiment is illustrated by the following operational example. It should be understood, however, that modifications and substitutions can be made without departing from the scope of this invention.

OPERATIONAL EXAMPLE

To prepare a disinfecting and gelling composition for treatment of aqueous medical wastes, three ingredients are employed:

1) Granular aggregates of dry glutaraldehyde, Thetford Corporation, Ann Arbor, Mich., (approximately 31% glutaraldehyde, 31% water, and 38% amorphous $SiO_2$ desiccant). The granules have a size distribution from 0.5 to 4 mm corresponding to a screen size of 6 to 30 mesh.

2) Superabsorbent granules comprising potassium or sodium polyacrylate, Chemdal Corp., trademarked respectively "Aridall 1440" and "Aridall 1465". The granules have a size distribution from 200 to 850 microns. The polyacrylate granules have been surface-treated with a polyquaternary amine to improve water-wetability.

3) The calcium silica desiccant sold as "Hubersorb 600", by J. M. Huber Corp. (average particle size 3.2 microns), or other similar non-swelling desiccant.

The foregoing ingredients are used in the following weight portions: 66% dry glutaraldehyde, 1% silicate desiccant, and 33% polyacrylate absorbent. The combining of the ingredient is carried out in a ribbon blender. The dry glutaraldehyde and the desiccant are first charged to the blender, which is rotated for 15 minutes in each direction. Preferably but not necessarily, the mixing is interrupted to remove a glutaraldehyde/desiccant pre-mix, which is stored in closed drums for several hours, viz. overnight or for 24 hours.

The acrylate polymer is introduced into the blender and the pre-mix of dry glutaraldehyde and desiccant is spread over the top of the polymer granules. The blender is then rotated for 15 minutes in each direction. In the first mixing operation, the dry glutaraldehyde aggregates have been partially reduced to a powder. In the second blending, the particles and remaining granules are brought into intimate contact with the acrylate polymer granules. Transfer of the glutaraldehyde can be visually observed by the appearance of a yellowish color associated with the previously white acrylate granules. Over-mixing should be avoided since it may generate heat and cause excessive transfer of moisture to the acrylate powder and granules. After a homogeneous mixture is obtained, the mixing is terminated. Optionally, if desired, a perfume may be added during the final mixing operation to mask the glutaraldehyde odor. For example 0.5% of a spray dried perfume can be used.

The product is ready for packaging and use. One ounce of the product can solidify and disinfect up to about 1500 milliliters of liquid waste, i.e. one part powder solidifies about fifty parts liquid (w/v). For example, a one ounce pre-measured quantity can be added to a liquid waste in a 1500 ml suction canister. Most of the mix will fall to the lower portion of the container, and then the liquid waste will be rapidly converted to a gelled body by the expansion of the polymer granules, which proceeds from the bottom to the top of the container. The glutaraldehyde disinfectant is distributed throughout the mass of the gelled body for effectively disinfecting the entire body. This distribution can be observed by the yellow color of the gelled material.

The disinfecting and gelling composition produced as described in this example is stable in storage. It remains free flowing despite the residual water in the dry glutaraldehyde material. In use, however, the glutaraldehyde remaining associated with the desiccant carrier is available for supplemental disinfection by diffusion into the aqueous medical waste. This product is useful for solidifying and disinfecting human and animal wastes resulting for medical or veterinary procedures and laboratory tests.

I claim:

1. A method of preparing a disinfecting and gelling composition, comprising the steps of:
   (a) selecting a free-flowing granular glutaraldehyde source material composed of non-swelling desiccant silica particles impregnated with a 25 to 75% aqueous solution of glutaraldehyde; and
   (b) mixing said granular glutaraldehyde material with free-flowing granules of a gel-forming superabsorbent, from 50 to 300 parts by weight of said glutaraldehyde material being present per 100 parts of said superabsorbent, said mixing blending the glutaraldehyde solution-containing particles with the superabsorbent granules, continuing said mixing until sufficient glutaraldehyde solution is transferred to said superabsorbent granules to impart a yellowish color thereto, then terminating said mixing before said superabsorbent granules become swollen to a non-free-flowing condition, thereby obtaining a stable admixture for effectively disinfecting and gelling aqueous wastes.

2. The composition prepared by the method of claim 1.

3. The method of claim 1 in which said superabsorbent is potassium polyacrylate.

4. The composition prepared by the method of claim 3.

5. A method of preparing a disinfecting and gelling composition, comprising the steps of:
   (a) selecting a free-flowing granular glutaraldehyde source material consisting of granular aggregates of non-swelling desiccant silica particles impregnated with a 25 to 75% aqueous solution of glutaraldehyde;
   (b) mixing said granular aggregates with a particulate non-swelling, non-impregnated desiccant, one part of desiccant being present per 40 to 100 parts of said aggregates, said mixing converting at least part of said aggregates to a powder and producing a free-flowing admixture; and
   (c) mixing said admixture with free-flowing granules of a gel-forming superabsorbent, from 50 to 300 parts of said glutaraldehyde material being present per 100 parts of superabsorbent, said mixing blending the glutaraldehyde solution-containing particles with the superabsorbent granules, continuing said mixing until sufficient glutaraldehyde solution is transferred to said superabsorbent granules to impart a yellowish color thereto, then terminating said mixing before said superabsorbent granules become swollen to a non-free flowing condition, thereby obtaining a stable admixture for effectively disinfecting and gelling aqueous wastes.

6. The composition produced by the method of claim 5.

7. The method of claim 5 in which the superabsorbent is potassium polyacrylate.

8. The composition produced by the method of claim 7.

* * * * *